(12) United States Patent
Parsheh et al.

(10) Patent No.: US 8,926,844 B2
(45) Date of Patent: Jan. 6, 2015

(54) SYSTEMS AND METHODS FOR PROCESSING ALGAE CULTIVATION FLUID

(75) Inventors: Mehran Parsheh, Castro Valley, CA (US); Megan Hippler, South Charleston, WV (US); Shahrokh A Naieni, Medina, WA (US); Guido Radaelli, San Carlos, CA (US)

(73) Assignee: Aurora Algae, Inc., Hayward, CA (US)

( * ) Notice: Subject to any disclaimer, the term of this patent is extended or adjusted under 35 U.S.C. 154(b) by 0 days.

(21) Appl. No.: 13/075,122

(22) Filed: Mar. 29, 2011

(65) Prior Publication Data

US 2011/0300568 A1    Dec. 8, 2011

(51) Int. Cl.
*C12Q 1/02* (2006.01)
*C12P 7/64* (2006.01)
*C12M 1/00* (2006.01)
*C12N 1/12* (2006.01)

(52) U.S. Cl.
CPC ............... *C12N 1/12* (2013.01); *C12P 7/6463* (2013.01); *Y02E 50/13* (2013.01); *C12M 29/18* (2013.01); *C12M 21/02* (2013.01); *C12M 29/26* (2013.01); *C12P 7/649* (2013.01); *Y10S 210/931* (2013.01)
USPC ...... 210/748.03; 210/605; 210/617; 210/151; 210/748.04; 210/931; 435/29; 435/257.1; 435/289.1; 435/292.1; 435/287.1; 422/186.07; 422/127; 429/513; 429/529

(58) Field of Classification Search
CPC ...... C12M 21/02; C12M 29/18; C12M 29/26; C12P 7/6463
USPC ......... 435/29, 257.1, 289.1, 292.1, 287.1, 41, 435/306.1; 210/605, 617, 151, 748.03, 210/748.04, 931; 422/186.04, 127; 204/157.15, 157.63, 275.1, 164; 429/513, 529, 197 R
See application file for complete search history.

(56) References Cited

U.S. PATENT DOCUMENTS

| | | | |
|---|---|---|---|
| 1,926,780 A | 9/1933 | Lippincott | |
| 2,730,190 A | 1/1956 | Brown et al. | |
| 2,766,203 A | 10/1956 | Brown et al. | |
| 3,175,687 A | 3/1965 | Jones | |

(Continued)

FOREIGN PATENT DOCUMENTS

| | | | |
|---|---|---|---|
| IN | 35/2013 A1 | 8/2013 | |
| JP | 09-024362 A | 1/1997 | |

(Continued)

OTHER PUBLICATIONS

Santin-Montanya, I. "Optimal Growth of Dunaliella Primolecta in Axenic Conditions to Assay Herbicides," Chemosphere, 66, Elsevier 2006, p. 1315-1322.

(Continued)

*Primary Examiner* — Walter D Griffin
*Assistant Examiner* — Cameron J Allen
(74) *Attorney, Agent, or Firm* — Carr & Ferrell LLP

(57) ABSTRACT

Systems and methods for reducing an amount of unwanted living organisms within an algae cultivation fluid are provided herein. According to some embodiments, methods may include subjecting the algae cultivation fluid to an amount of cavitation, the amount of cavitation being defined by a pressure differential between a downstream pressure and a vapor pressure, the pressure differential divided by half of a product of a fluid density multiplied by a square of a velocity of an apparatus throat.

16 Claims, 15 Drawing Sheets

(56) References Cited

U.S. PATENT DOCUMENTS

| | | | |
|---|---|---|---|
| 3,468,057 A | 9/1969 | Buisson et al. | |
| 3,897,000 A | 7/1975 | Mandt | |
| 3,962,466 A | 6/1976 | Nakabayashi | |
| 4,003,337 A | 1/1977 | Moore | |
| 4,065,875 A * | 1/1978 | Srna | 47/1.4 |
| 4,159,944 A * | 7/1979 | Erickson et al. | 210/611 |
| 4,253,271 A | 3/1981 | Raymond | |
| 4,267,038 A | 5/1981 | Thompson | |
| 4,341,038 A | 7/1982 | Bloch et al. | |
| 4,365,938 A | 12/1982 | Warinner | |
| 4,535,060 A | 8/1985 | Comai | |
| 4,658,757 A | 4/1987 | Cook | |
| 5,105,085 A | 4/1992 | McGuire et al. | |
| 5,130,242 A | 7/1992 | Barclay | |
| 5,180,499 A | 1/1993 | Hinson et al. | |
| 5,244,921 A | 9/1993 | Kyle et al. | |
| 5,275,732 A | 1/1994 | Wang et al. | |
| 5,338,673 A | 8/1994 | Thepenier et al. | |
| 5,478,208 A | 12/1995 | Kasai et al. | |
| 5,527,456 A | 6/1996 | Jensen | |
| 5,539,133 A | 7/1996 | Kohn et al. | |
| 5,567,732 A | 10/1996 | Kyle et al. | |
| 5,658,767 A | 8/1997 | Kyle | |
| 5,661,017 A | 8/1997 | Dunahay et al. | |
| 5,668,298 A | 9/1997 | Waldron | |
| 5,776,349 A | 7/1998 | Guelcher et al. | |
| 6,117,313 A | 9/2000 | Goldman et al. | |
| 6,143,562 A | 11/2000 | Trulson et al. | |
| 6,166,231 A | 12/2000 | Hoeksema | |
| 6,372,460 B1 | 4/2002 | Gladue et al. | |
| 6,524,486 B2 | 2/2003 | Borodyanski et al. | |
| 6,579,714 B1 | 6/2003 | Hirabayashi et al. | |
| 6,736,572 B2 | 5/2004 | Geraghty | |
| 6,750,048 B2 | 6/2004 | Ruecker et al. | |
| 6,768,015 B1 | 7/2004 | Luxem et al. | |
| 6,831,040 B1 | 12/2004 | Unkefer et al. | |
| 7,381,326 B2 | 6/2008 | Haddas | |
| 7,582,784 B2 | 9/2009 | Banavali et al. | |
| 7,767,837 B2 | 8/2010 | Elliott | |
| 7,868,195 B2 | 1/2011 | Fleischer et al. | |
| 7,883,882 B2 | 2/2011 | Franklin et al. | |
| 8,088,614 B2 | 1/2012 | Vick et al. | |
| 8,404,473 B2 | 3/2013 | Kilian et al. | |
| 8,569,530 B2 | 10/2013 | Hippler et al. | |
| 2003/0199490 A1 | 10/2003 | Antoni-Zimmermann et al. | |
| 2004/0121447 A1 | 6/2004 | Fournier | |
| 2004/0161364 A1 | 8/2004 | Carlson | |
| 2004/0262219 A1 | 12/2004 | Jensen | |
| 2005/0048474 A1 | 3/2005 | Amburgey, Jr. | |
| 2005/0064577 A1 | 3/2005 | Berzin | |
| 2005/0164192 A1 | 7/2005 | Graham et al. | |
| 2005/0170479 A1 | 8/2005 | Weaver et al. | |
| 2005/0260553 A1 | 11/2005 | Berzin | |
| 2005/0273885 A1 | 12/2005 | Singh et al. | |
| 2006/0045750 A1 | 3/2006 | Stiles | |
| 2006/0101535 A1 | 5/2006 | Forster et al. | |
| 2006/0122410 A1 | 6/2006 | Fichtali et al. | |
| 2006/0166243 A1 | 7/2006 | Su et al. | |
| 2007/0102371 A1 * | 5/2007 | Bhalchandra et al. | 210/748 |
| 2008/0118964 A1 | 5/2008 | Huntley et al. | |
| 2008/0120749 A1 | 5/2008 | Melis et al. | |
| 2008/0155888 A1 | 7/2008 | Vick et al. | |
| 2008/0160591 A1 | 7/2008 | Willson et al. | |
| 2008/0160593 A1 | 7/2008 | Oyler | |
| 2008/0194029 A1 | 8/2008 | Hegemann et al. | |
| 2008/0268302 A1 * | 10/2008 | McCall | 429/17 |
| 2008/0275260 A1 | 11/2008 | Elliott | |
| 2008/0293132 A1 | 11/2008 | Goldman et al. | |
| 2009/0011492 A1 | 1/2009 | Berzin | |
| 2009/0029445 A1 | 1/2009 | Eckelberry et al. | |
| 2009/0081748 A1 | 3/2009 | Oyler | |
| 2009/0148931 A1 | 6/2009 | Wilkerson et al. | |
| 2009/0151241 A1 | 6/2009 | Dressler et al. | |
| 2009/0162919 A1 | 6/2009 | Radaelli et al. | |
| 2009/0234146 A1 | 9/2009 | Cooney et al. | |
| 2009/0317857 A1 | 12/2009 | Vick et al. | |
| 2009/0317878 A1 | 12/2009 | Champagne et al. | |
| 2009/0317904 A1 | 12/2009 | Vick et al. | |
| 2009/0325270 A1 | 12/2009 | Vick et al. | |
| 2010/0022393 A1 | 1/2010 | Vick | |
| 2010/0068772 A1 * | 3/2010 | Downey | 435/134 |
| 2010/0151540 A1 | 6/2010 | Gordon et al. | |
| 2010/0183744 A1 | 7/2010 | Weissman et al. | |
| 2010/0196995 A1 | 8/2010 | Weissman et al. | |
| 2010/0210003 A1 | 8/2010 | King et al. | |
| 2010/0210832 A1 | 8/2010 | Kilian et al. | |
| 2010/0260618 A1 | 10/2010 | Parsheh et al. | |
| 2010/0261922 A1 | 10/2010 | Fleischer et al. | |
| 2010/0314324 A1 | 12/2010 | Rice et al. | |
| 2010/0317088 A1 | 12/2010 | Radaelli et al. | |
| 2010/0327077 A1 | 12/2010 | Parsheh et al. | |
| 2010/0330643 A1 | 12/2010 | Kilian et al. | |
| 2010/0330658 A1 | 12/2010 | Fleischer et al. | |
| 2011/0041386 A1 | 2/2011 | Fleischer et al. | |
| 2011/0070639 A1 * | 3/2011 | Pandit et al. | 435/306.1 |
| 2011/0072713 A1 | 3/2011 | Fleischer et al. | |
| 2011/0136212 A1 | 6/2011 | Parsheh et al. | |
| 2011/0196163 A1 | 8/2011 | Fleischer et al. | |
| 2011/0197306 A1 | 8/2011 | Bailey et al. | |
| 2011/0300568 A1 | 12/2011 | Parsheh et al. | |
| 2011/0313181 A1 | 12/2011 | Thompson et al. | |
| 2012/0129244 A1 * | 5/2012 | Green et al. | 435/257.1 |
| 2013/0274490 A1 | 10/2013 | Hippler et al. | |

FOREIGN PATENT DOCUMENTS

| | | |
|---|---|---|
| JP | 2004300218 | 10/2004 |
| JP | 2008280252 | 11/2008 |
| WO | 2004106238 A2 | 12/2004 |
| WO | 2008060571 A2 | 5/2008 |
| WO | 2009037683 A1 | 3/2009 |
| WO | 2009082696 A1 | 7/2009 |
| WO | 2011053867 A1 | 5/2011 |

OTHER PUBLICATIONS

Felix, R. "Use of the cell wall-less alga Dunaliella bioculata in herbicide screening tests," Annals of Applied Biology, 113, 1988, pp. 55-60.

Janssen, M. "Phytosynthetic efficiency of Dunaliella tertiolecta under short light/dark cycles," Enzyme and Microbial Technology, 29, 2001, p. 298-305.

Saenz, M.E., "Effects of Technical Grade and a Commercial Formulation of Glyphosate on Algal Population Growth," Bulletin of Environmental Contamination Toxicology, 1997, 59: pates 638-644.

Endo et al. "Inactivation of Blasticidin S by Bacillus cereus II. Isolation and Characterization of a Plasmid, pBSR 8, from Bacillus cereus," The Journal of Antibiotics 41 (2): 271-2589-2601, Feb. 1988.

Hallmann et al., "Genetic Engineering of the Multicellular Green Alga Volvox: A Modified and Multiplied Bacterial Antibiotic Resistance Gene as a Dominant Selectable Marker" The Plant Journal 17(1): 99-109 (Jan. 1999).

Kindle et al. "Stable Nuclear Transformation of Chlamydomonas Using the Chlamydomonas Gene for Nitrate Reductase" The Journal of Cell Biology 109 (6, part 1) 1989: 2589-2601.

Prein et al. "A Novel Strategy for Constructing N-Terminal Chromosomal Fusions to Green Fluorescent Protein in the Yeast Saccharomyces cerevisiae" FEBS Letters 485 (2000) 29-34.

Schiedlmeier et al., "Nuclear Transformation of Volvox Carteri" Proceedings of the National Academy of Sciences USA 91(11): 5080-5084 (May 1994).

Wendland et al. "PCR-Based Methods Facilitate Targeted Gene Manipulations and Cloning Procedures" Curr.Gen. (2003) 44:115-123.

Molnar et al., "Highly Specific Gene Silencing by Artificial MicroRNAs in the Unicellular Agla Chlamydomonas reinhardtii," Plant Jour. ePub Jan. 17, 2009, vol. 58, No. 1, pp. 157-164 (Abstract Only).

(56) References Cited

OTHER PUBLICATIONS

Chen et al., "Conditional Production of a Functional Fish Growth Hormone in the Transgenic Line of Nannochloropsis oculata (Eustigmatophyceae)," J. Phycol. Jun. 2008, vol. 44, No. 3, pp. 768-776.
Nelson et al., "Targeted Disruption of NIT8 Gene in Chlamydomonas reinhardtii." Mol. Cell. Bio. Oct. 1995, vol. 15, No. 10, pp. 5762-5769.
Grima et al. "Recovery of Microalgal Biomass in Metabolites: Process Options and Economics," Biotechnology Advances 20, 2003, pp. 491-515.
Knuckey et al. "Production of Microalgal Concentrates by Flocculation and their Assessment as Aquaculture Feeds," Aquacultural Engineering 35, 2006, pp. 300-313.
Kureshy et al., "Effect of Ozone Treatment on Cultures of Nannochloropsis oculata, Isochrysis galbana, and Chaetoceros gracilis," Journal of the World Aquaculture Society, 1999, 30(4), pp. 473-480.
Csogor et al., "Light Distribution in a Novel Photobioreactor—Modelling for Optimization," Journal of Applied Phycology, vol. 13, 2001, pp. 325-333.
Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.
Zittelli et al., "Mass Cultivation of Nannochloropsis Sp. in Annular Reactors," Journal of Applied Phycology, vol. 15, pp. 107-113, Mar. 2003.
Strzepek et al., "Photosynthetic Architecture Differs in Coastal and Oceanic Diatoms," Nature, vol. 431, pp. 689-692, Oct. 2004.
Lee et al., "Isolation and Characterization of a Xanthophyll Aberrant Mutant of the Green Alga Nannochloropsis oculata," Marine Biotechnology, 2006, vol. 8, pp. 238-245.
NCBI entry EE109892 (Jul. 2006) [Retrieved from the Internet on Oct. 19, 2009, <http://www.ncbi.nlm.nih.gov/nucest/EE109892?ordinalops=1&itool=EntrezSystem2.Pentrez.Sequence.Sequence_ResultsPanel.Sequence_RVDocSum>].
Berberoglu et al., "Radiation Characteristics of Chlamydomonas reinhardtii CC125 and its truncated chlorophyll antenna transformants tla1, tlaX, and tla1-CW+," International Journal of Hydrogen Energy, 2008, vol. 33, pp. 6467-6483.
Ghirardi et al., "Photochemical Apparatus Organization in the Thylakoid Membrane of Hordeum vulgare wild type and chlorophyll b-less chlorina f2 mutant," Biochimica et Biophysica Act (BBA)—Bioengergetics, vol. 851, Issue 3, Oct. 1986, pp. 331-339 (abstract only).
Steinitz et al., "A mutant of the cyanobacterium Plectonema boryanum resistant to photooxidation," Plant Science Letters, vol. 16, Issues 2-3, 1979, pp. 327-335 (abstract only).
Koller et al., "Light Intensity During Leaf Growth Affects Chlorophyll Concentration and CO2 Assimilation of a Soybean Chlorophyll Mutant," Crop Science, 1974, vol. 14, pp. 779-782 (abstract only).
Shikanai et al., "Identification and Characterization of *Arabidopsis* Mutants with Reduced Quenching of Chlorophyll Fluorescence," Plant and Cell Physiology, 1999, vol. 40, No. 11, pp. 1134-1142 (abstract only).
Hedenskog, G. et al., "Investigation of Some Methods for Increasing the Digestibility in Vitro of Microalgae," Biotechnology and Bioengineering, vol. XI, pp. 37-51, 1969.

Loury, "Method for Rapid Conversion of Fats to Methyl Esters," Revue Francaise des Corps Gras, 1967, 14(6), 383-389 (abstract only).
Cravotto et al., "Improved Extraction of Vegetable Oils under high-intensity Ultrasound and/or Microwaves," Ultrasonics Sonochemistry, 15: 898-902, 2008.
Ben-Amotz, Ami. "Large-Scale Open Algae Ponds," presented at the NREL-AFOSR Joint Workshop on Algal Oil for Get Fuel Production in Feb. 2008.
Ebeling et al., "Design and Operation of a Zero-Exchange Mixed-Cell Raceway Production System," 2nd Int'l Sustainable Marine Fish Culture Conference and Workshop, Oct. 2005.
Ebeling et al., "Mixed-Cell Raceway: Engineering Design Criteria, Construction, and Hydraulic Characterization," North American Journal of Aquaculture, 2005, 67: 193-201 (abstract only).
Labatut et al., "Hydrodynamics of a Large-Scale Mixed-Cell Raceway (MCR): Experimental Studies," Aquacultural Engineering vol. 37, Issue 2, Sep. 2007, pp. 132-143.
Kizilisoley et al., "Micro-Algae Growth Technology Systems," Presented by Selim Helacioglu, Soley Institute, 2008.
Dunstan et al., "Changes in the Lipid Composition and Maximisation of the Polyunsaturated Fatty Acid Content of Three Microalgae Grown in Mass Culture," Journal of Applied Phycology, 5, pp. 71-83, 1993.
Carvalheiro et al., "Hemicellulose Biorefineries: A Review on Biomass Pretreatments," Journal of Scientific & Industrial Research, vol. 67, Nov. 2008, pp. 849-864.
Lotero et al., "Synthesis of Biodiesel via Acid Catalysis," Ind. Eng. Chem. Res., 2005, pp. 5353-5363.
Gouveia et al., "Microalgae as a raw material for biofuels production," J. Ind. Microbiol. Biotechnol, 2009, vol. 36, 269-274.
International Search Report and Written Opinion of the International Searching Authority mailed Jan. 6, 2011 for Application No. PCT/US2010/054861, filed Oct. 29, 2010.
Chen et al., "Subcritical co-solvents extraction of lipid from wet microalgae pastes of Nannochloropsis sp.," Eur. J. Lipid Sci. Technol., vol. 114, 2012, pp. 205-212.
Wang et al., "Lipid and Biomass Distribution and Recovery from Two Microalgae by Aqueous and Alcohol Processing," Journal of the American Oil Chemists' Society, vol. 38, Issue 2, Jul. 2011, pp. 335-345.
Pitipanapong et al., "New approach for extraction of charantin from Momordica charantia with pressurized liquid extraction," Separation and Purification Technology, vol. 52, Issue 3, Jan. 2007.
International Search Report and Written Opinion of the International Searching Authority mailed Feb. 5, 2009 for Application No. PCT/US2008/087722, filed Dec. 19, 2008.
Examination Report mailed Aug. 15, 2013 in Australian Application No. 2010313246 filed Oct. 29, 2010.
Second Examination Report mailed Dec. 17, 2013 in Australian Application No. 2010313246 filed Oct. 29, 2010.
Lubian, L. M., "Concentrating Cultured Marine Microalgae with Chitosan." Aquaculture Engineering, 8, 257-265 (1989).
Divakaran, R. & Sivasankara Pillai, VN, "Flocculation of Algae Using Chitosan." Journal of Applied Phycology, 14, 419-422 (2002).
Farid, M. S., Shariati, A., Badakhshan, A., & Anvaripour, B., "Using Nano-Chitosan for Harvesting Microalga Nannochloropsis sp." Bioresource Technology, 131, 555-559 (2013).

* cited by examiner

SYSTEMS AND METHODS FOR PROCESSING ALGAE CULTIVATION FLUID

BACKGROUND OF THE INVENTION

1. Field of the Invention

The present invention relates generally to systems and methods for processing algae cultivation fluid, and more particularly, to systems and methods adapted to reduce an amount of unwanted living organisms within an algae cultivation fluid. According to some embodiments, the systems and methods may be adapted to reduce an amount of unwanted living organisms within the algae cultivation fluid to more efficiently produce algae cells that are utilized in the manufacture of products such as biodiesel fuel.

2. Description of Related Art

Algae cells are typically grown in open-air systems, such as raceway reactors, and/or in closed systems, such as photo-bioreactors, which may utilize tanks. Because raceway reactors are open to the elements, the algae cells contained therein are highly susceptible to contamination from unwanted living organisms such as bacteria and or other living organisms that consume the algae cells or compete with the algae cells for nutrients. It will be understood that the terms "unwanted living organisms" may also be known generically as "grazers," because of their propensity to consume the algae cells, the nutrients that the algae cells consume, or both. Photo-bioreactors, while less likely to be contaminated with grazers because they are closed systems, are substantially more expensive to manufacture and maintain than raceway reactors.

It will be understood that because the algae cells within the algae cultivation fluid require sunlight to drive photosynthesis, algae cells growing near the surface of the algae cultivation fluid may aggregate and block the sunlight needed by algae cells disposed below. As such, the algae cultivation fluid may be mixed or otherwise communicated to help distribute the sunlight through the algae cultivation fluid.

If the algae cells within the algae cultivation fluid are provided sufficient sunlight, inorganic chemicals, and or other beneficial minerals (e.g., nitrogen, potassium, phosphorous, etc.), the algae cells may proliferate and may be harvested via any suitable method that would be known to one of ordinary skill in the art with the present disclosure before them. Therefore, it is desirable that unwanted living organisms that may compete with the algae cells for food (e.g., minerals and inorganic chemicals) or directly consume the algae cells should be substantially reduced, if not completely eliminated. If the population of unwanted living organisms within the algae cultivation fluid is not controlled, issues relative to the collapse of algae cell populations may occur. For example, the unwanted living organisms may consume the algae cells, leading to a crash of the pond. In general, the term "crash" may indicate that over time, the amount of algae cells may decrease to a point where the pond does not have enough algae cells for the predators to consume, so that the predators die off. Therefore, the systems and methods disclosed herein are adapted to reduce the amount of unwanted living organisms within the algae cultivation fluid.

SUMMARY OF THE INVENTION

Provided herein are exemplary systems and methods for processing algae cultivation fluid. Exemplary methods for reducing an amount of unwanted living organisms within an algae cultivation fluid may include the step of subjecting the algae cultivation fluid to an amount of cavitation, the amount of cavitation being defined by (or related to) a pressure differential between a downstream static pressure and a vapor pressure, the pressure differential divided by half of a product of a fluid density multiplied by a square of a velocity of an apparatus throat.

According to other embodiments, methods for reducing an amount of unwanted living organisms within an algae cultivation fluid may include passing the algae cultivation fluid through at least one apparatus throat to induce an amount of cavitation within the algae cultivation fluid to reduce the unwanted living organisms within the algae cultivation fluid.

In additional embodiments, systems for reducing an amount of unwanted living organisms within an algae cultivation fluid may include: (a) an algae cultivation fluid source for receiving and retaining an algae cultivation fluid; (b) a cavitation apparatus in fluid communication with the algae cultivation fluid source; and (c) a fluid motive source adapted to communicate the algae cultivation fluid into the cavitation apparatus with sufficient velocity to induce an amount of cavitation within the algae cultivation fluid by passing the algae cultivation fluid through the cavitation apparatus.

According to some exemplary embodiments, an improved method for producing a biofuel from algae cultivation fluid may include at least the steps of: (a) passing the algae cultivation fluid through at least one apparatus throat to induce an amount of cavitation within the algae cultivation fluid to reduce the unwanted living organisms within the algae cultivation fluid; (b) wherein reducing the amount of unwanted living organisms within an algae cultivation fluid causes algae cells within the algae cultivation fluid to mature at an accelerated rate relative to algae cells within algae cultivation fluid having a higher concentration of unwanted living organisms; (c) separating mature algae cells from the algae cultivation fluid; and (d) processing the mature algae cells in such a way that biofuel is produced.

BRIEF DESCRIPTION OF THE DRAWINGS

Certain embodiments of the present invention are illustrated by the accompanying figures. It will be understood that the figures are not necessarily to scale and that details (e.g., dimensions) not necessary for an understanding of the invention or that render other details difficult to perceive may be omitted. It will be understood that the invention is not necessarily limited to the particular embodiments illustrated herein.

DETAILED DESCRIPTION

Figure 1A:
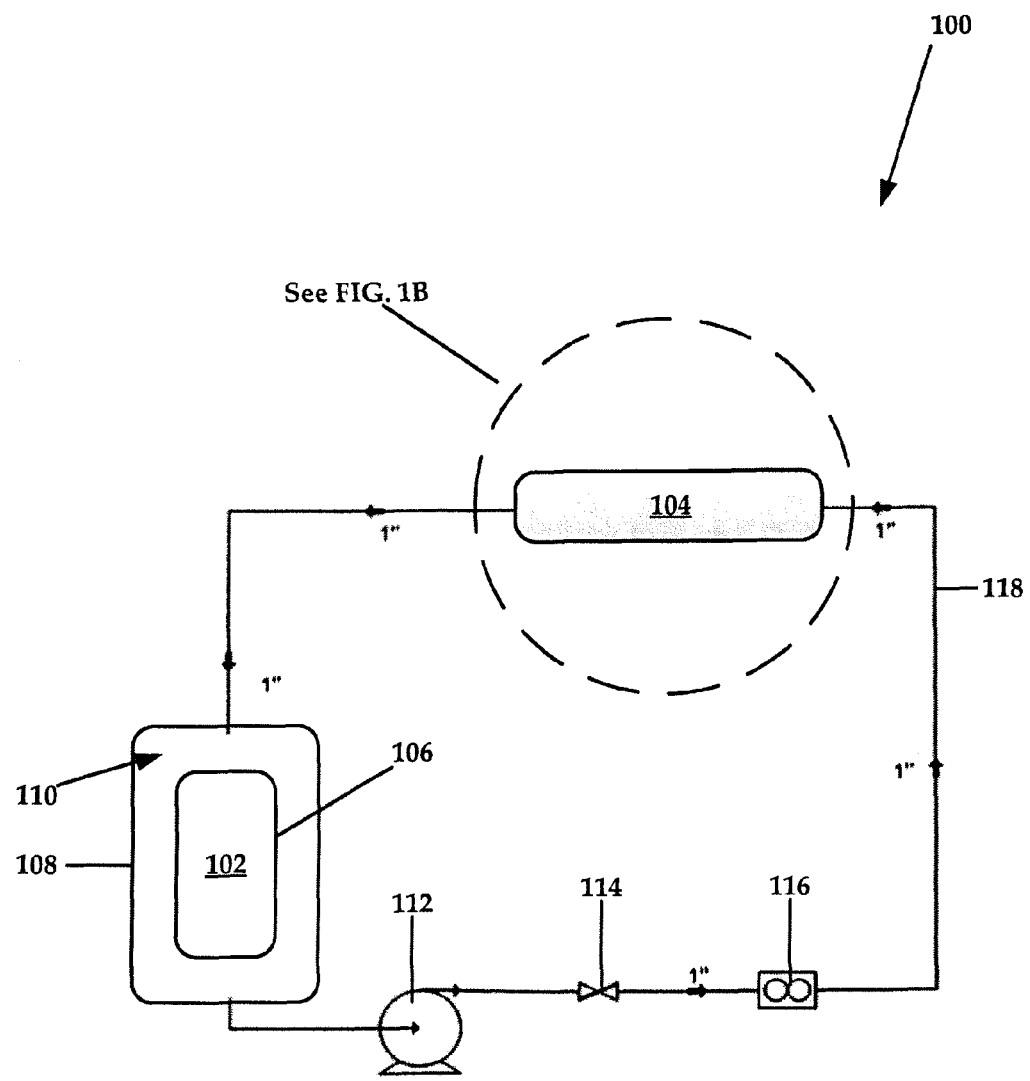
FIG. 1A of the drawings is a schematic diagram of an exemplary system for processing algae cultivation fluid, constructed in accordance with the present invention.

The systems and methods provided herein are adapted to reduce the amount of unwanted living organisms within algae cultivation fluid by cavitating the algae cultivation fluid as the algae cultivation fluid passes through a cavitation device. Generally speaking, cavitation may be defined as the formation of gas bubbles of a flowing fluid (e.g., algae cultivation fluid) in a region, typically within a restriction, where the static pressure of the flowing fluid falls below its vapor pressure. The process of cavitation includes the inception, growth, and eventual collapse of gas bubbles created by a decrease in the static pressure of flowing fluid.

The processed algae cultivation fluid may be utilized to produce algae cells that may be utilized in the manufacture of products such as biodiesel, bioplastics, dyes and colorants, fertilizers, animal feedstock, various pharmaceuticals, nutraceuticals, and the like. Algae cells may also be produced to help aid in pollution control, as algae consume carbon dioxide. It will be understood that the algae cells within the algae cultivation fluid may include, for example algae of genus *nannochloropsis*.

The systems described herein may be adapted to receive algae cultivation fluid from one or more raceway reactors and pass the algae cultivation fluid through a cavitation apparatus to induce an amount of cavitation in the algae cultivation fluid. The induced cavitation reduces the amount of unwanted living organisms within the algae cultivation fluid. The processed algae cultivation fluid is then returned to one or more raceway reactors.

It will be understood that the amount of cavitation induced in the algae cultivation fluid may be directly correlated to the amount of reduction of unwanted living organisms within the algae cultivation fluid and/or the type of unwanted living organisms within the algae cultivation fluid.

The amount of cavitation induced in the algae cultivation fluid may be represented by a cavitation number $\sigma$ that is defined by the formula below and described in greater detail infra:

$$\sigma = \frac{P_d - P_v}{0.5\rho U^2}.$$

The cavitation number $\sigma$ is defined as the difference of a downstream static pressure $P_d$ of the algae cultivation fluid and a vapor pressure $P_v$ of the algae cultivation fluid divided by one half of the product of a density $\rho$ of the algae cultivation fluid and a square of a velocity $U$ of the algae cultivation fluid in the throat of the cavitation device.

In practice, a cavitation number falling approximately within a range of 0.05 to 1 may reduce the amount of unwanted living organisms within the algae cultivation fluid by a specific amount. It will be understood that the lower the cavitation number $\sigma$ is, the greater the reduction in the amount of unwanted living organisms as a result of higher cavitation intensity. Conversely, as the cavitation number $\sigma$ increases, the lower the reduction in the amount of unwanted living organisms as a result of the lower cavitation intensity. It is noteworthy that as the cavitation number $\sigma$ is decreased, the greater the likelihood that algae cells within the algae cultivation fluid may be damaged along with the unwanted living organisms.

Selectively varying one or more of the variables of the equation indicative of the algae cultivation fluid may selectively modify the cavitation number of the algae cultivation fluid. For example, to decrease the cavitation number $\sigma$, the velocity $U$ of the algae cultivation fluid through the cavitation apparatus throat may be increased causing a decrease in the pressure inside of the throat.

It is noteworthy that there appears to be a limitation to decreasing the cavitation number $\sigma$, in that by decreasing the downstream static pressure $P_d$ may choke the flow of the algae cultivation fluid through the cavitation apparatus (if the cavitation apparatus includes a venturi-type device). Choked flow is a limiting condition seen in compressible fluids. Generally speaking, this choked flow phenomenon occurs when the flow rate of the algae cultivation fluid passing through the venturi-type device will not increase with a further decrease in the downstream static pressure. This phenomenon assumes that the upstream pressure of the algae cultivation fluid is fixed. Moreover, as some of the cavitation apparatuses disclosed herein may incorporate venturi-type devices, it will be understood that the flow rate of algae cultivation fluid through choked venturi-type devices causes underperformance of the venturi-type device and poor overall performance of the cavitation apparatus.

The cavitation induced in the algae cultivation fluid may reduce the amount of unwanted living organisms within the algae cultivation fluid by any one of a number (or combination) of effects including, but not limited to, the production of free radicals within the algae cultivation fluid via processes such as homolysis. The free radicals produced by the induction of cavitation are cytotoxic to some types of unwanted living organisms.

Additionally, the shockwave produced by collapsing gas bubbles within the cavitating flow may destroy or impair some unwanted living organisms. For example, one exemplary genus of unwanted living organisms includes monas guttula (also referred to as "Monas"), which includes organisms that have motive sources such as flagellum and/or cilium. The shockwaves may sever the motive sources from the organisms thereby rendering them immobile and unable to feed. After a specified period of time, the organisms die off.

After the collapse of the bubbles downstream of the device, a substantial amount of turbulent kinetic energy is generated. As a result of shear generated by the turbulent fluctuations, the grazers are generally ripped apart.

Commonly encountered unwanted living organisms may include non-limiting examples such as rotifers, cryptomonads, larval copepods, gnathostomulids, monerans, or other similar protists, along with various types of spirotrichs such as euplotes. One of ordinary skill in the art will appreciate that many other types of unwanted living organisms may likewise be susceptible to damage via the induction of cavitation within the algae cultivation fluid.

Referring now to the drawings, and more particularly, to FIG. 1A, which includes a perspective view of a system 100 for processing algae cultivation fluid. The system 100 may be broadly described as including an algae cultivation fluid source, hereinafter referred to as "raceway reactor 102," and a cavitation apparatus 104. The raceway reactor 102 may be fabricated having both inner and outer peripheral walls 106 and 108 joined together via a lower wall (not shown) providing separation of the raceway reactor 102 from the ground below. The inner and outer walls 106 and 108 may be spaced apart from one another to define an annular pathway 110 for receiving and retaining the algae cultivation fluid.

Although not shown, the system may also include additional hydraulic devices such as pumps, nozzles, mixers such as static mixers and paddles, which cause a mixing of the algae cultivation fluid as it communicates around the annular pathway 110. Mixing of the algae cultivation fluid allows sunlight to be distributed to all the algae within the algae cultivation fluid. It will be understood that although the present disclosure contemplates the use of a raceway reactor 102, one of ordinary skill in the art will appreciate that many other types of algae reactors, such as photobioreactors, may likewise be utilized in accordance with the present invention.

According to some embodiments, the system 100 may also include one or more fluid motive sources 112 such as a pump, adapted to communicate the algae cultivation fluid through the system 100. The system 100 may also include a valve 114 adapted to selectively control the flow rate of the algae cultivation fluid. Additionally, a sensing device 116 such as a flow meter may be disposed downstream of the valve 114 to monitor the flow rate of the algae cultivation fluid exiting the valve 114. It will be understood that monitoring the output of the sensing device 116 provides a basis for the selective adjustment of the flow rate of the algae cultivation fluid by opening or closing the valve 114 or selectively varying the output of the fluid motive source 112.

It is noteworthy that each of the components of the system 100 are operatively connected via a conduit 118 that may include any one of hoses, pipes, ducts, channels, or combinations thereof.

Figure 1B:
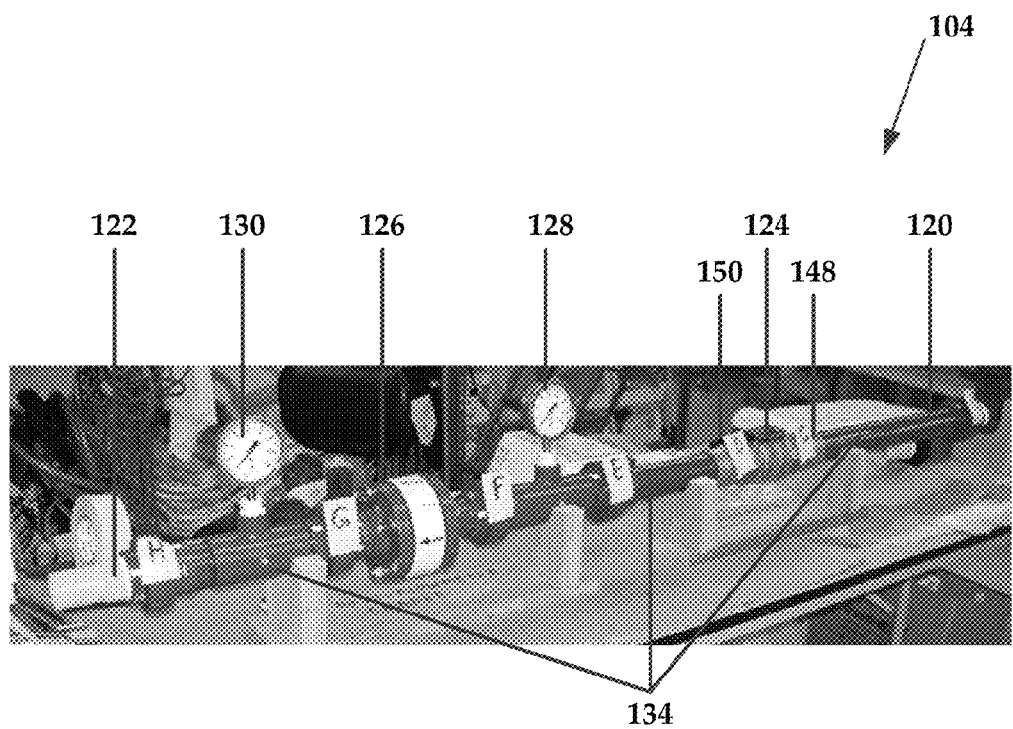
FIG. 1B of the drawings is a perspective view of a cavitation apparatus for inducing an amount of cavitation within algae cultivation fluid passing therethrough.

Referring now to FIGS. 1A and 1B collectively, the cavitation apparatus 104 may be generally described as having a plurality of components including an inlet 120, an outlet 122, a first cavitation unit 124, a second cavitation unit 126, and first and second pressure gauges 128 and 130, respectively. Broadly speaking, each of the components of the cavitation apparatus 104 may be interconnected in series via sections of tubular piping 134 such that the first cavitation unit 124 is disposed downstream of the inlet 120 and the first pressure gauge 128 is disposed downstream of the first cavitation unit 124.

The second cavitation unit 126 may be disposed downstream of the first pressure gauge 128 and the second pressure gauge 130 may be disposed downstream of the second cavitation unit 126 followed by the outlet 122.

The inlet 120 of the cavitation apparatus 104 may be adapted to receive algae cultivation fluid from the raceway reactor 102 via the conduit 118. The inlet 120 may operatively couple to the conduit 118 via any one of a number of different ways such as clamps, threaded couplings, compression fittings, and unions—just to name a few. The inlet 120 may also be operatively coupled to the first cavitation unit 124.

Figure 1C:
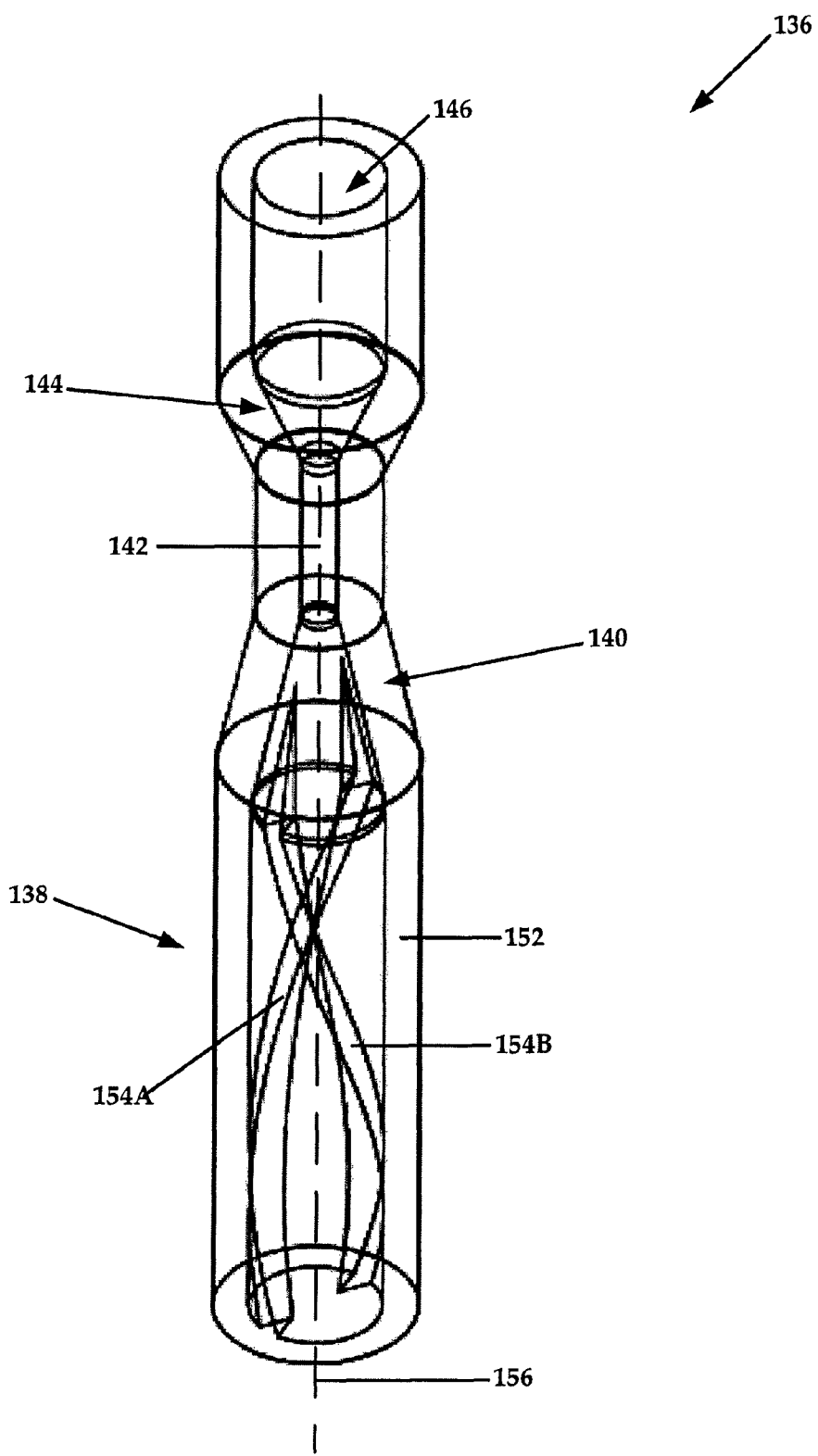
FIG. 1C of the drawings is a transparent isometric view of a venturi-type device having a rifled inlet section.
Figure 1D:
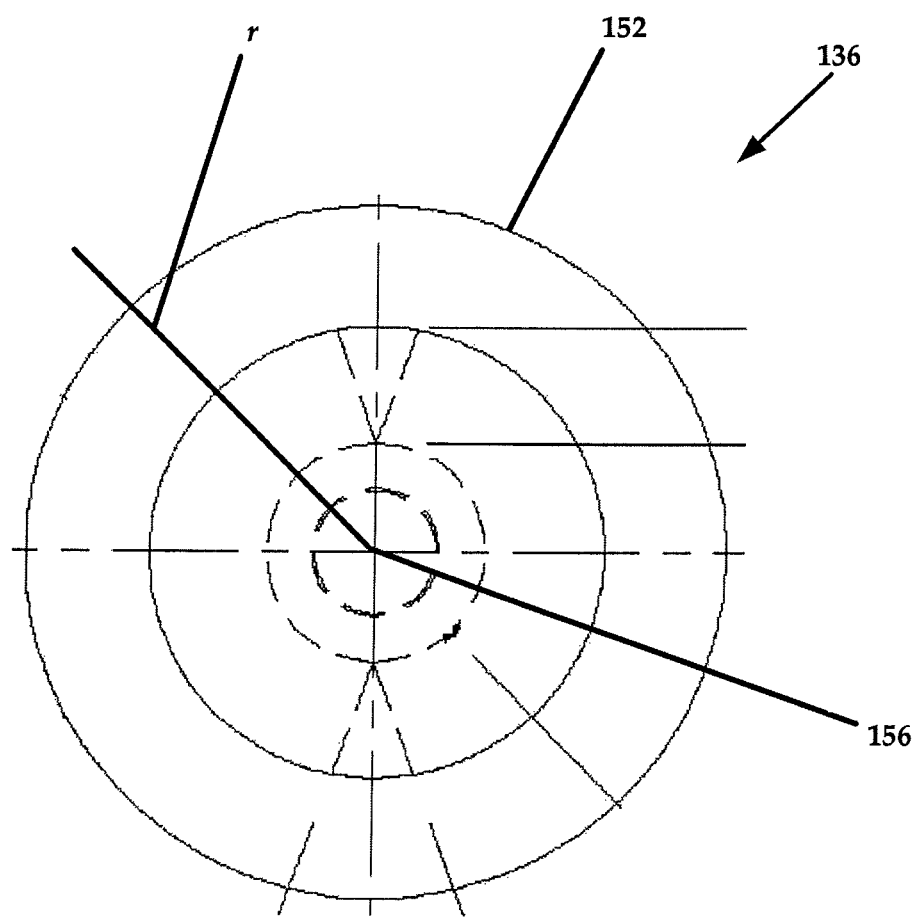
FIG. 1D of the drawings is an end view of the venturi-type device of FIG. 1C showing the rifled inlet section.

Referring now to FIGS. 1C and 1D collectively, according to some embodiments, the first cavitation unit 124 may include a venturi-type device 136. The venturi-type device 136 may include a rifled inlet section 138 extending to a convergent nozzle 140. The venturi-type device 136 may also include a venturi throat 142 (also known as an apparatus throat) positioned between the convergent nozzle 140 and a divergent nozzle 144 that extends to a smoothbore outlet 146.

The venturi-type device 136 may be operatively connected to the inlet 120 via a first union 148 (see FIG. 1B) and to one section of the tubular piping 134 associated with the first pressure gauge 128 via a second union 150 (also see FIG. 1B).

The rifled inlet section 138 may include a cylindrical body 152 having one or more helical vanes extending therethrough and around a central axis 156. According to some embodiments, two helical vanes 154A and 154B extend in a double helix pattern along the length of the cylindrical body. In some embodiments, the helical vanes 154A and 154B extend at least partially into the convergent nozzle 140.

Each of the two vanes extend away from an inner sidewall of the cylindrical body 152 at an angle relative to a radial axis r (see FIG. 1D) extending from the central axis 156 of the cylindrical body 152 to the inner sidewall of the cylindrical body 152. As the algae cultivation fluid communicates through the cylindrical body 152, the algae cultivation fluid is caused to swirl around the central axis 156 and generate a vortex with the axis in the streamline direction as it enters the convergent nozzle 140. The swirling of algae cultivation fluid causes a decrease in static pressure at the center of the generated vortex in the algae cultivation fluid before introduction into the venturi throat 142 via the convergent nozzle 140.

One of ordinary skill in the art will appreciate that the cylindrical body 152 may include any number of helical vanes 154 that cause the algae cultivation fluid to swirl within the cylindrical body 152 and produce a desired static pressure reduction of the algae cultivation fluid. Additionally, although not shown, rather than including helical vanes, the cylindrical body 152 may include alternating helical sidewalls that extend along the length of the cylindrical body 152 spaced apart from one another to define helical grooves that are adapted to cause the algae cultivation fluid to swirl as it communicates through the cylindrical body 152.

The convergent nozzle 140 includes a substantially frustoconical geometrical configuration that transitions from a larger diameter proximate the rifled inlet section 138 to a smaller diameter proximate the apparatus throat 142. This reduction in diameter causes an increase in the velocity of the algae cultivation fluid and a subsequent drop in the static pressure of the algae cultivation fluid as it passes therethrough. It will be understood that the drop in static pressure of the algae cultivation fluid may be of sufficient magnitude to bring the downstream pressure below the vapor pressure.

The majority of induction and growth of gas bubbles resulting from the induction of cavitation by the venturi-type device 136 occurs within the apparatus throat 142. The venturi throat 142 is provided with a diameter that may be approximately the same diameter as the smaller diameter of the rifled inlet section 138. The diameter of the apparatus throat 142 may be uniform along the length of the apparatus throat 142.

Algae cultivation fluid exiting the venturi throat 142 passes into the divergent nozzle 144 and ultimately into the smoothbore outlet 146. Expanding gas bubbles formed in the algae cultivation fluid collapse as the velocity of the algae cultivation fluid decreases, and the static pressure of the algae cultivation fluid increases, causing a reduction in the amount of unwanted living organisms within the algae cultivation fluid by the shockwaves produced by the collapse of the gas bubbles, free radical generation and/or the large amount of shear due to the high intensity turbulence.

Figure 1E:
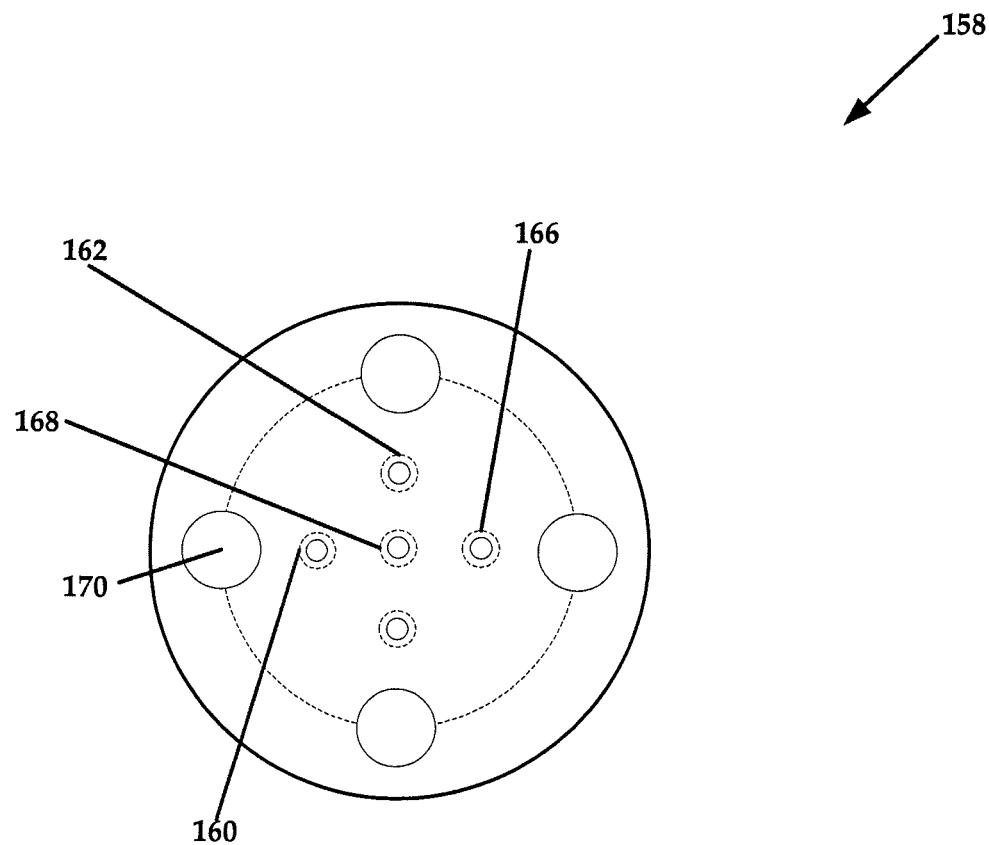
FIG. 1E of the drawings is a front elevational view of an orifice plate.
Figure 1F:
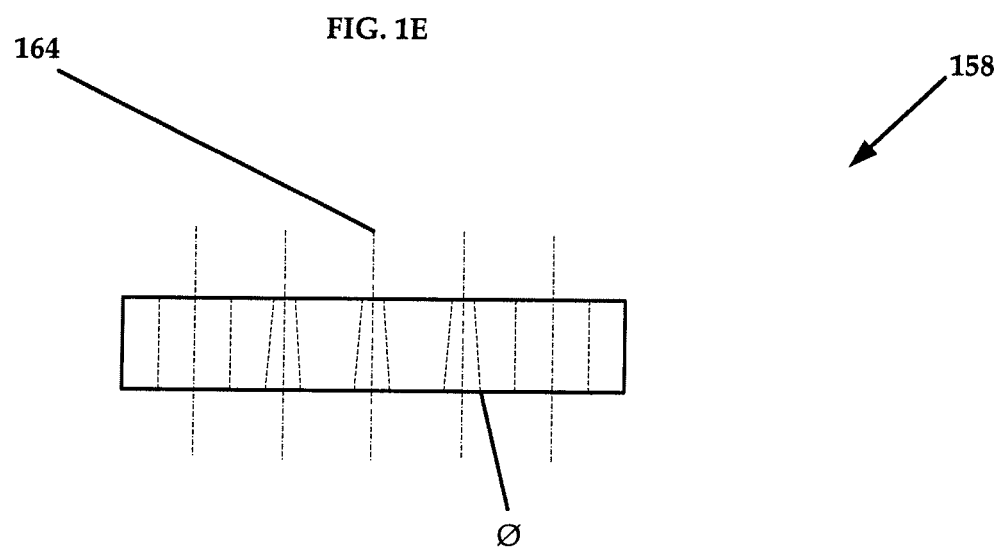
FIG. 1F of the drawings is a top plan view of the orifice plate of FIG. 1E.

Referring now to FIGS. 1E and 1F collectively, shown therein is an orifice plate 158 of the second cavitation unit 126. The second cavitation unit 126 may be disposed downstream of the first cavitation unit 124 and operatively connected to another section of the tubular piping 134 associated with the second pressure gauge 130. According to some embodiments, the orifice plate 158 may be fabricated from a strong and resilient material such as a metal, metallic alloy, or a polymeric material. Moreover, the orifice plate 158 may be fabricated as a monolithic component having one or more orifices. According to some embodiments, the orifice plate 158 may have a substantially uniform thickness ranging from approximately four to fifty millimeters.

In some embodiments, the orifice plate 158 may include a horizontal axis 160 and a vertical axis 162 that intersect one another, along with a central axis 164 (FIG. 1F) that is disposed at the intersection point between the horizontal and vertical axes. The orifice plate 158 may include four intermediate orifices 166 (note that only one of the four intermediate orifices 166 has been labeled on FIG. 1E) disposed around a central orifice 168. It will be understood that each of the orifices may also be referred to as an "apparatus throat." Additionally, orifice plates may have anywhere from one, two, three, four, five and upward (i.e. unlimited) number of orifices.

The four intermediate orifices 166 may be disposed in a circular pattern around the orifice plate 158 such that each of the four intermediate orifices 166 is spaced apart from adjacent portions of the horizontal axis 160 and the vertical axis 162 by approximately 45 degrees. Moreover, each of the four intermediate orifices 166 may be disposed at a radial length of approximately 5.7 millimeters from the central axis 164. Additionally, in some embodiments, there is no limitation for radial length, as it can be dependent on the size of the plate.

According to some embodiments, the central orifice 168 may have a substantially frusto-conical geometrical configuration having a larger diameter transitioning to a smaller diameter downstream. According to some embodiments, the frusto-conical configuration may be defined by an angle Ø of the inner sidewall of the central orifice 168 of approximately 20 degrees relative to central axis 164. It will be understood that each of the four intermediate orifices 166 may be configured similarly to the central orifice 168.

The central orifice 168 is disposed in substantial axial alignment with the central axis 164 of the orifice plate 158. Both the four intermediate orifices 166 and the central orifice 168 have substantially identical diameters, which in some embodiments may be approximately three millimeters.

The reduction in diameter of the orifices cause the velocity of the algae cultivation fluid passing through the orifices to increase, thereby decreasing the static pressure of the algae cultivation fluid. Moreover, the shape of the orifices may generate less energy loss than cylindrical orifices without angled sidewalls. The energy loss of cavitation units will be discussed in greater detail infra. Similarly to the venturi-type device 136 (see FIGS. 1C and 1D), an amount of cavitation is induced in the four intermediate orifices 166 and the central orifice 168 (collective known as the apparatus throats) to reduce the amount of unwanted living organisms within the algae cultivation fluid.

It is noteworthy that the amount of cavitation produced by the orifice plate 158 may be selectively controlled by varying the flowrate of the algae cultivation fluid passing through the orifices of the orifice plate 158.

The orifice plate 158 may also include a plurality of apertures 170 disposed in a substantially arcuate pattern around the orifice plate at a radial length that is longer than the radial length of the four intermediate orifices 166. The apertures 170 may each be adapted to receive a bolt for joining the orifice plate to opposing flanges (not shown) associated with tubular sections on opposing ends of the second cavitation unit 126.

Figure 1G:
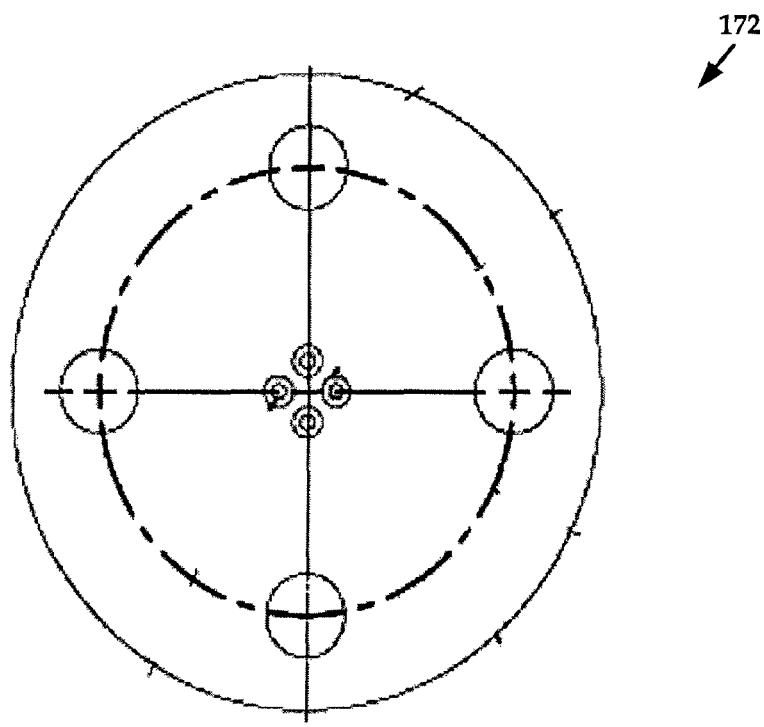
FIG. 1G of the drawings is a front elevational view of an alternative exemplary orifice plate.
Figure 1H:
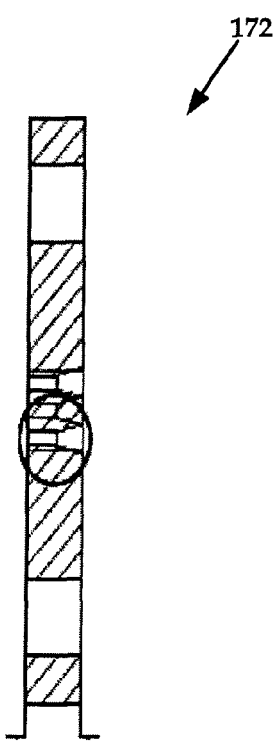
FIG. 1H is a top plan view of the orifice plate of FIG. 1G.

FIG. 1G of the drawings is a front elevational view of an alternative exemplary orifice plate 172. FIG. 1H is a top plan view of the orifice plate 172 of FIG. 1G.

Figure 1I:
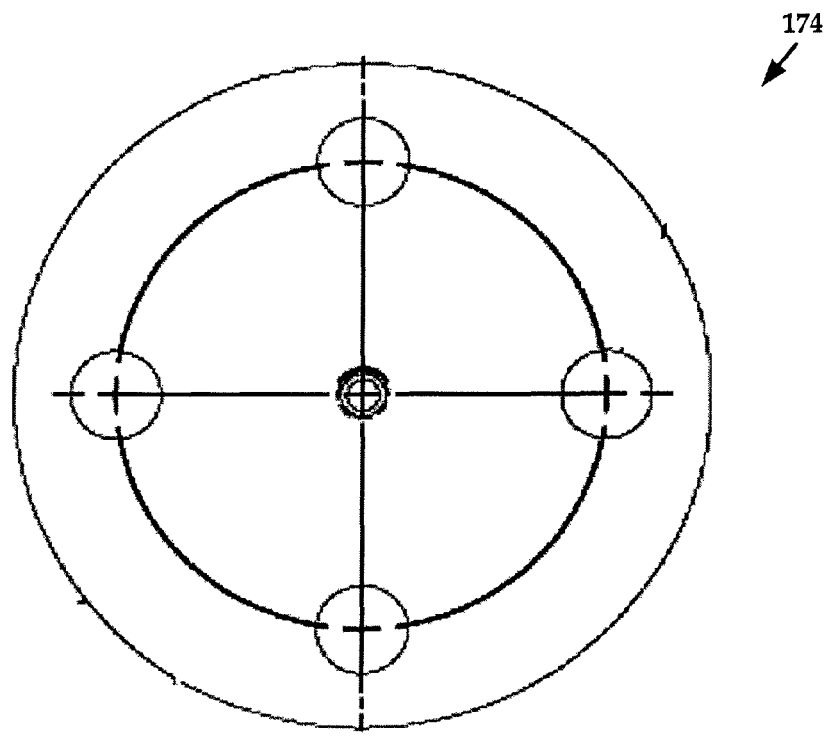
FIG. 1I of the drawings is a front elevational view of another exemplary orifice plate.
Figure 1J:
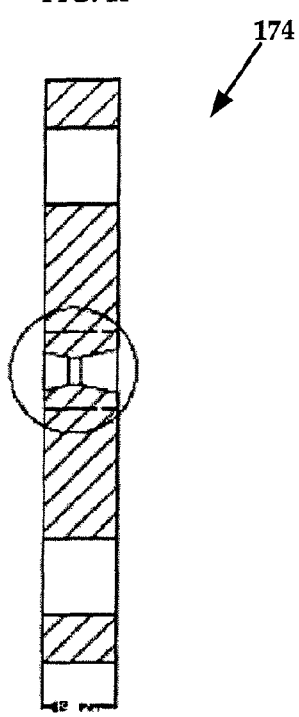
FIG. 1J is a top plan view of the orifice plate of FIG. 1I.

FIG. 1I of the drawings is a front elevational view of another exemplary orifice plate 174. FIG. 1J is a top plan view of the orifice plate 174 of FIG. 1I.

Figure 1K:
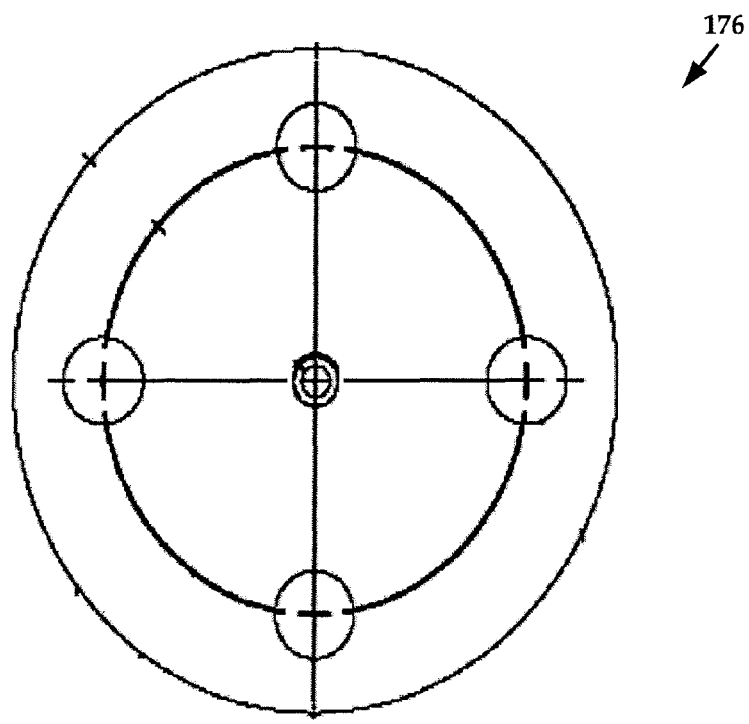
FIG. 1K of the drawings is a front elevational view of yet another exemplary orifice plate.
Figure 1L:
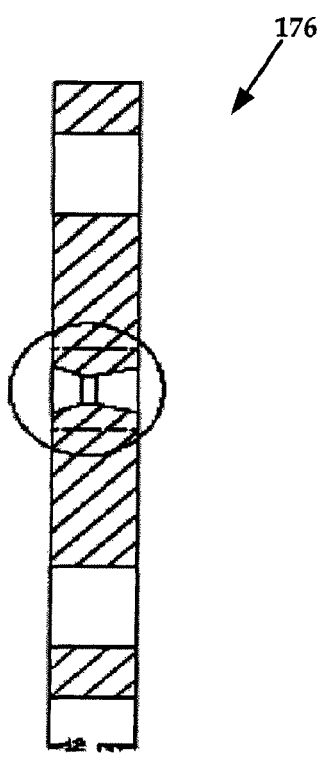
FIG. 1L is a top plan view of the orifice plate of FIG. 1K.

FIG. 1K of the drawings is a front elevational view of yet another exemplary orifice plate 176. FIG. 1L is a top plan view of the orifice plate 176 of FIG. 1K.

Referring now to FIGS. 1A-1L collectively, the second cavitation unit 126 may be operatively connected to the outlet 122 of the cavitation apparatus 104, which is in turn connected to the conduit 118 that provides the processed algae cultivation fluid back to the raceway reactor 102.

While it has been disclosed that the cavitation apparatus 104 includes first and second cavitation units 124 and 126, respectively, it will be understood that the cavitation unit 104 may include any number of cavitation units. Moreover, the cavitation units may include any of an orifice plate, a venturi-type device (having rifled inlet sections or not), or other any other device adapted to induce a sufficient amount of cavitation within the algae cultivation fluid to reduce the amount of unwanted living organisms within the algae cultivation fluid. Additionally, in some embodiments, it is possible to integrate two or more cavitation devices into a single unit.

In operation, the motive source 112 is engaged to draw algae cultivation fluid from the raceway reactor 102 via the conduit 118. The algae cultivation fluid is communicated through the valve 114 and past the sensing device 116 (e.g., flow meter), into the inlet 120 of the cavitation apparatus 104. The algae cultivation fluid is communicated into the rifled inlet section 138 of the venturi-type device 136 and begins to swirl around the central axis 156 of the cylindrical body 152 of the rifled inlet section 138.

As the algae cultivation fluid passes through the venturi-type device 136, an amount of cavitation is induced within the algae cultivation flowing fluid. Gas bubbles formed during the induction of cavitation may collapse downstream from the first cavitation unit 124 reducing the amount of unwanted living organisms within the algae cultivation fluid by a given amount.

The algae cultivation fluid then communicates into the second cavitation unit 126 and across the orifice plate 158. As the algae cultivation fluid passes through the four intermediate orifices 166 and the central orifice 168, an amount of cavitation is induced within the algae cultivation fluid. Gas bubbles formed during the induction of cavitation may collapse downstream from the second cavitation unit 126, reducing the amount of unwanted living organisms within the algae cultivation fluid by another amount.

The algae cultivation fluid may then communicate from the outlet 122 of the cavitation apparatus 104 back to the annular pathway 110 of the raceway reactor 102 via the conduit 118. The communication of the algae cultivation fluid back to the raceway reactor 102 may also create an amount of mixing within the raceway reactor 102, allowing sunlight to filter more evenly through the algae cultivation fluid. In some cases, the treated algae cultivation fluid may be transported to a clean, empty pond.

The downstream static pressure (which is a function of the throat dimensions and flowrate) of the algae cultivation fluid may be measured to determine the efficiency of each of the cavitation units of the cavitation apparatus 104 by way of the first and second pressure gauges 128 and 130 disposed downstream of the first and second cavitation units 124 and 126, respectively.

Additionally, the flowrate of the algae cultivation fluid may be selectively controlled to induce the desired amount of cavitation within the algae cultivation fluid.

The amount of cavitation produced by the cavitation apparatus 104 may directly relate to the type of unwanted living organisms present with the algae cultivation fluid. For example, rotifers may be substantially removed from the algae cultivation fluid at cavitation numbers of approximately 0.65 while Monas may require cavitation numbers within a range as low as 0.15 to 0.17. Therefore, before operation of the system 100, it may be advantageous to determine the type of unwanted living organisms present within the algae cultivation fluid.

It will be understood that the type of cavitation unit (e.g., plate orifice, venturi-type device, rifled venturi-type device, or combinations thereof) selected to induce an amount of cavitation within the algae cultivation fluid may be influenced by the flowrate of the algae cultivation fluid that is required to produce sufficient pressure reductions through the cavitation unit. Higher flowrates are the direct result of higher energy consumption by the fluid motive source 112. Therefore, cavitation units may be selected, which both produce sufficient reductions in the amount of unwanted living organisms and operate at sufficiently low energy consumption rates to produce the reduction.

As such, the efficiency of a cavitation unit may be represented by an orifice discharge coefficient, which may be defined as the loss of energy of the flow of algae cultivation fluid through a cavitation unit. It will be understood that "through a cavitation unit" may specifically refer to the algae cultivation fluid passing through the apparatus throat of the cavitation unit. Moreover, the upstream pressure and flow relationship of the cavitation unit may be related according to the following equation:

$$P = \frac{1}{2}\rho\frac{U^2}{c_d^2},$$

where P is the static pressure upstream of the orifice. The percentage of energy loss, $E_L$, through the cavitation unit is defined by the following equation:

$$E_L = (1 - c_d^2) \times 100.$$

For example, suppose a 64 percent loss of the flow energy is seen in the orifice. For a perfect cavitation unit, the discharge coefficient is equal to one. For a cavitation unit that includes a sharp orifice, the discharge coefficient may include an approximate range of discharge coefficients from 0.6 to 0.65. From the energy loss equation provided above, it is clear that in order to decrease the pressure of the motive fluid source 112, very efficient (e.g., having discharge coefficients approaching one) orifices and venturi-type devices should be selected.

Exemplary Use Case for a Single Venturi-Type Device

A first micropond D4 was contaminated with 36,000 Monas per milliliter. In order to test the performance of various cavitation devices and associated cavitation numbers, half of the algae cultivation fluid in micropond D4 was transported to a second micropond D3. After the transfer was complete, both miroponds D4 and D3 were filled to a 15 centimeter level using a dilutive fluid. This process was repeated for each cavitation device and associated cavitation number.

Table 1 (below) shows the experimental conditions and results. Specifically, Table 1 shows cavitation number and associated cavitation device identifier, flowrate in gallons per minute, pressure in pounds per square inch, kill rate, Monas after treatment, Monas five hours after treatment, and Monas 18 hours after treatment. Table 2 (below) shows cavitation device specifications by specific cavitation plate or cavitation venturi. Table 2 includes throat area in square millimeters, number of holes, throat length in square millimeters, contracting angle in degrees, divergence angle in degrees, discharge coefficient, and percentage of energy loss.

Kill rate as shown in Table 1 is defined as:

$$k_r = \frac{M_p - M_s}{M_p} \times 100$$

where $M_p$ is the number of Monas present within the algae cultivation fluid before treatment, and $M_s$ is the number of Monas in the algae cultivation fluid after treatment (that survived processing). It should be understood that the kill rate with respect to Monas may also be applied to the kill rate with respect to other predators or grazers.

As shown in Table 1, the kill rate immediately after the tests were performed was generally less than 71%. The inventors observed that the diluted algae cultivation fluid in the second micropond D3 was substantially free of contamination, having only a few stunned Monas. On the subsequent day, the inventors observed that the second micropond D3 was free of Monas. At this same time, the inventors observed that the first micropond D4 had 7,250 Monas per milliliter. The inventors also observed that micropond D3 was clean of Monas in the following days. This delayed kill effect is probably due to the damage to the grazers, the effect of dilution when micropond D3 was filled to a 15 centimeters level after the testing, and/or due to the effect of free radicals that take time to kill the predators after testing.

TABLE 1

| Cavitation Number and Device Identifier | Flowrate [gallons per minute] | Pressure [pounds per square inch] | Kill Rate | Monas after Treatment | After 5 hours | After 8 hours |
| --- | --- | --- | --- | --- | --- | --- |
| 0.208 (Plate FL4) | 8.35 | 174 | 70% | 30% Stunned | Not Moving | Disappeared |
| 0.208 (Plate FL6) | 8.35 | 170 | 67% | 33% Stunned | Not Moving | Disappeared |
| 0.221 (Plate FL2) | 8.3 | 160 | 66% | 39% Stunned | Not Moving | Some moving |
| 0.217 (Plate FL3) | 8.18 | 172 | 66% | 34% Stunned | Not Moving | Some moving |
| 0.330 (Plate FL1) | 12.25 | 113 | 12% | 88% Stunned | Not Moving | Disappeared |
| 0.336 (Plate FL6) | 7 | 105 | 37% | 63% Stunned | Not Moving | Some Moving |

TABLE 1-continued

| Cavitation Number and Device Identifier | Flowrate [gallons per minute] | Pressure [pounds per square inch] | Kill Rate | Monas after Treatment | After 5 hours | After 8 hours |
| --- | --- | --- | --- | --- | --- | --- |
| 0.526 (Plate FL6) | 5.25 | 60 | 45% | Some moving | Some Moving | Some Moving |
| 0.20 (Rifle Venturi) | 13.89 | 78 | 47% | 53% Stunned | Some Moving | Some Moving |
| Valve | 7.82 | 180 | 47% | 53% Stunned | No Moving | Moving |

TABLE 2

| Plate (FL) or Venturi | Throat Area [mm$^2$] | Number of Holes | Throat Length [mm] | Contracting Angle degrees | Divergence Angle Degrees | Discharge Coefficient | Percentage of Energy Loss |
| --- | --- | --- | --- | --- | --- | --- | --- |
| FL1 | 31.65 | 1 | 8 | NA | 20 | 0.617 | 61.9% |
| FL3 | 17.34 | 1 | 6 | NA | 12 | 0.610 | 62.8% |
| FL4 | 17.34 | 2 | 6 | NA | 12 | 0.621 | 61.4% |
| FL5 | 17.34 | 3 | 6 | NA | 12 | 0.621 | 61.4% |
| FL6 | 17.34 | 4 | 6 | NA | 12 | 0.626 | 60.8% |
| FL2 | 17.34 | 5 | 6 | NA | 12 | 0.629 | 60.4% |
| FL8 | 17.34 | 1 | 2 | 12 | 12 | 0.851 | 27.6% |
| FL9 | 17.34 | 1 | 2 | 20 | 20 | 0.826 | 31.8% |
| FL10 | 17.34 | 1 | 4 | 20 | 12 | 0.818 | 33% |
| Rifle Venturi | 28.26 | 1 | 25 | NA | 10.8 | 0.944 | 10.8% |
| Venturi V1 | 38.47 | 1 | 35 | NA | 19.1 | Not Tested | Not Tested |

Figure 2:
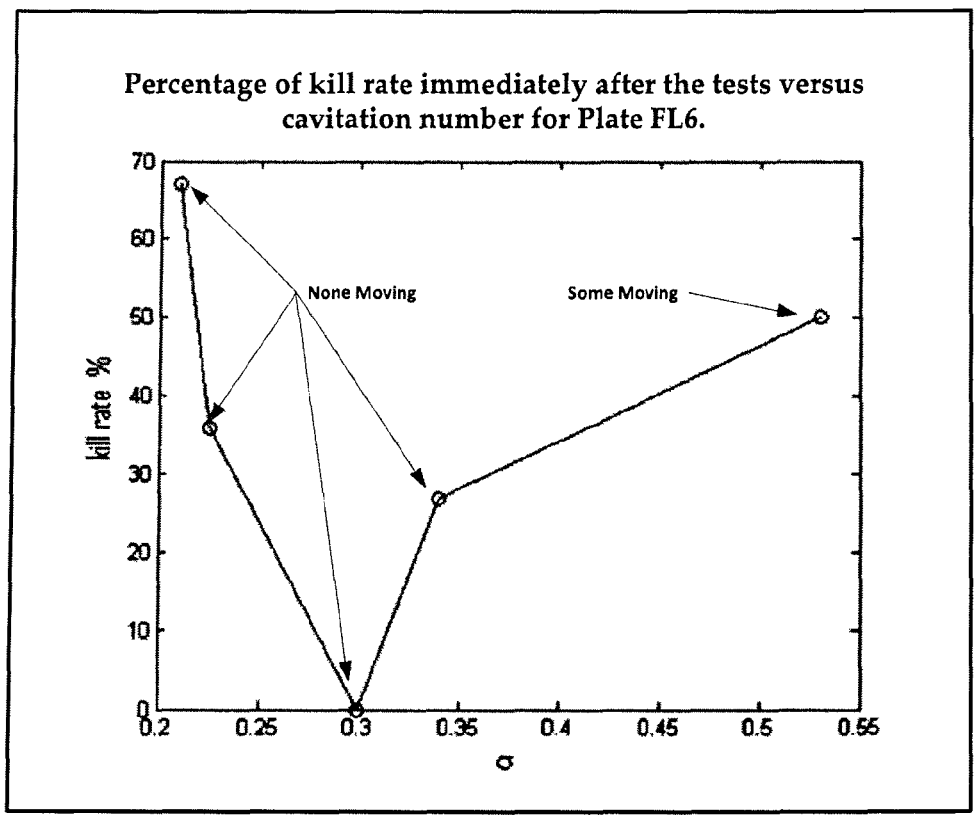
FIG. 2 of the drawings is a graph showing a kill rate of Monas versus cavitation number.

FIG. 2 shows the variation in kill rate versus cavitation number immediately after the test for plate FL6 was performed (as shown in Table 1).

Figure 3:
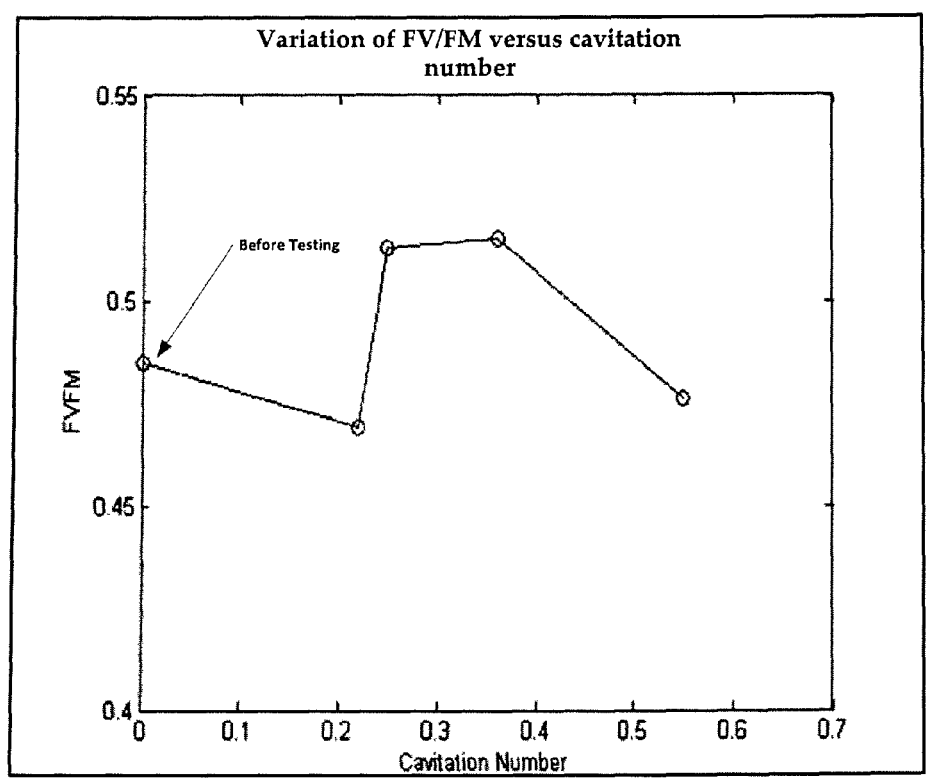
FIG. 3 of the drawings is a graph showing FV/FM versus cavitation number.

FIG. 3 of the drawings is a graph showing FV/FM versus cavitation number. Fv/Fm is a measure of the efficiency of photosystem II photochemistry. Fv/Fm is proportional to the quantum yield of photosynthesis. It is interesting to note that no significant variation in FV/FM versus the cavitation number was observed. In some embodiments, FV/FM may be a function of time rather than the cavitation intensity and/or the cavitation number.

Exemplary Use Case with Two Venturi-Type Devices

Tests were performed with two venturi-type cavitation devices placed in series. On the first day, half of the contaminated algae cultivation fluid in a first micropond D4 was untreated and diluted for future use. On the second day, this micropond D4 had 7,500 Monas per milliliter. One third of the volume of the algae cultivation fluid in micropond D4 was processed using two venturi-type devices in series (one of the venturi-type devices included a rifled inlet section). The processed algae cultivation fluid was drained and samples were retained for future evaluation.

Figure 4:
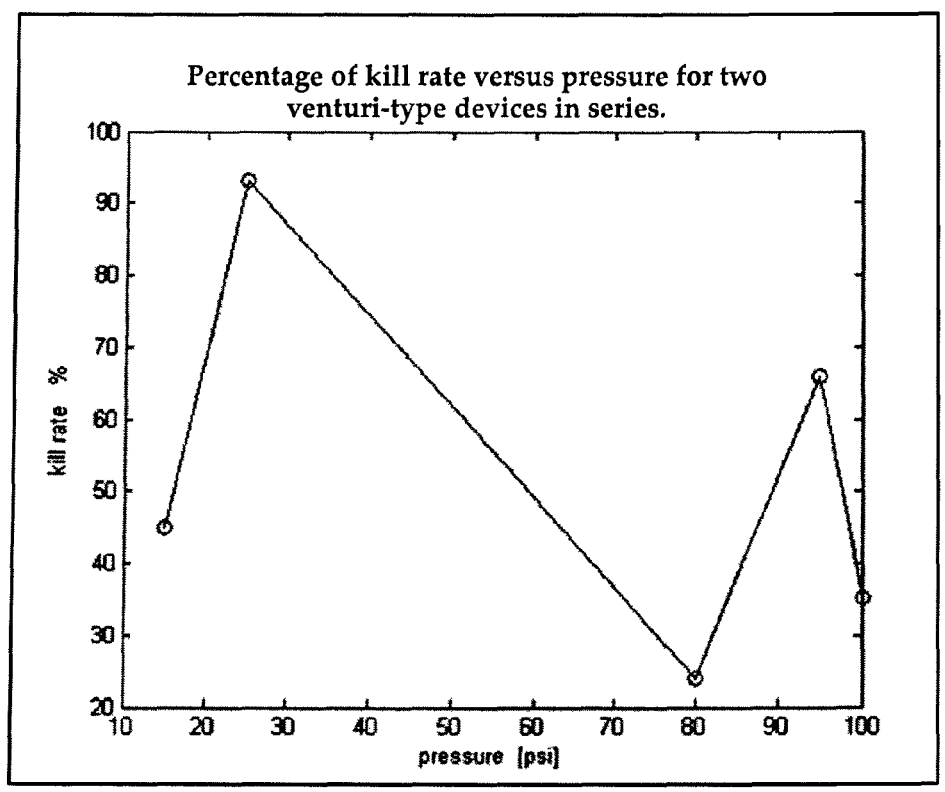
FIG. 4 of the drawings is a graph showing kill rate percentage versus upstream pressure for two cavitation devices in series.

FIG. 4 is a graph showing kill rate percentage versus upstream pressure for the two venture-type cavitation devices in series. For the experimental results shown in FIG. 4, the venturi throat sizes for the two venturi-type devices were different, which made it difficult if not impossible to define a cavitation number. Therefore, the results shown in FIG. 4 are plotted as kill rates in percentages versus plate upstream pressure. The inventors observed that the discharge coefficient of the series was 0.77 versus 0.93 for the venturi-type device having the rifle inlet section alone.

Productivity Tests of Healthy Algae

A first micropond D4 had 41,500 Monas per milliliter and 250 per milliliter of euplotes. A venturi-type cavitation device having a rifled inlet section was used to transfer algae cultivation fluid from the first micropond D4 to a second micropond D3 and to third micropond MP5 based on the following flow characteristics: one third of the volume of the first micropond D4 to the second micropond D3 at a pressure of 31 pounds per square inch, a flow rate of 9.05 gallons per minute, and a cavitation number of 0.45; one third of the volume of the first micropond D4 to the third micropond MP5 at a pressure of 46 pounds per square inch, a flow rate of 10.9 gallons per minute, and a cavitation number of 0.33; and one third of the first micropond D4 remained in the first micropond D4. All of the microponds were filled to 15 centimeters with a dilutive fluid.

Figure 5:
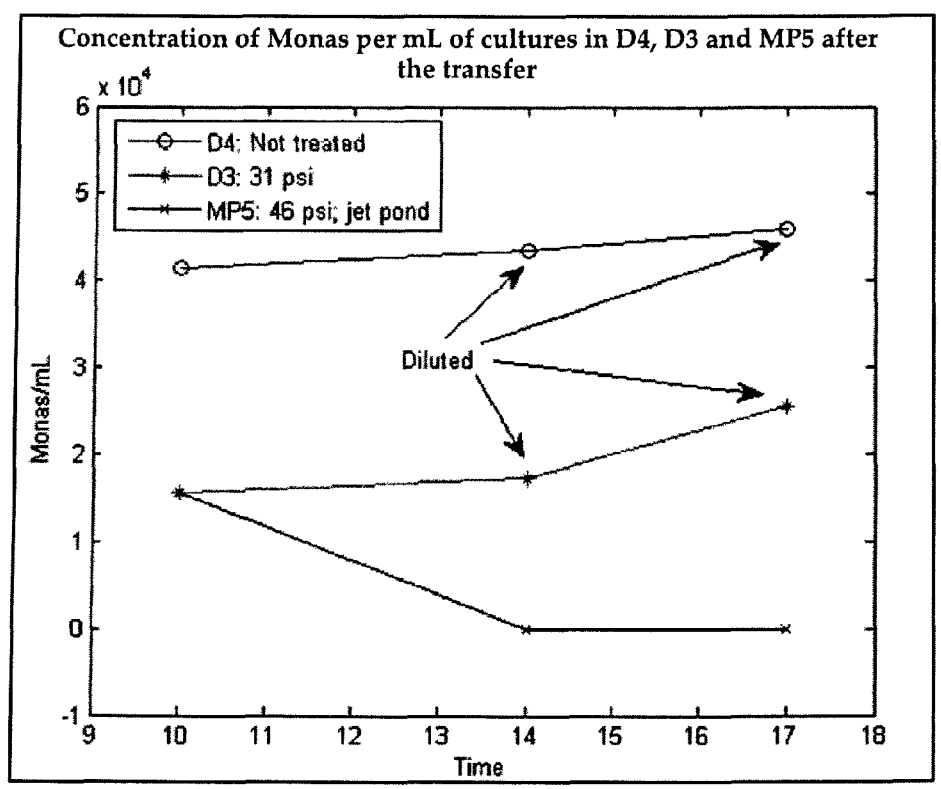
FIG. 5 of the drawings is a graph showing concentration of Monas per milliliter of culture versus time.

FIG. 5 of the drawings is a graph showing concentration of Monas per milliliter of culture versus time for the first micropond D4, the second micropond D3, and the third micropond MP5 (as described above). The inventors observed that the third micropond MP5 was free of Monas, and that the second micropond D3 and the first micropond D4 were still contaminated with a significant amount of Monas.

Figure 6:
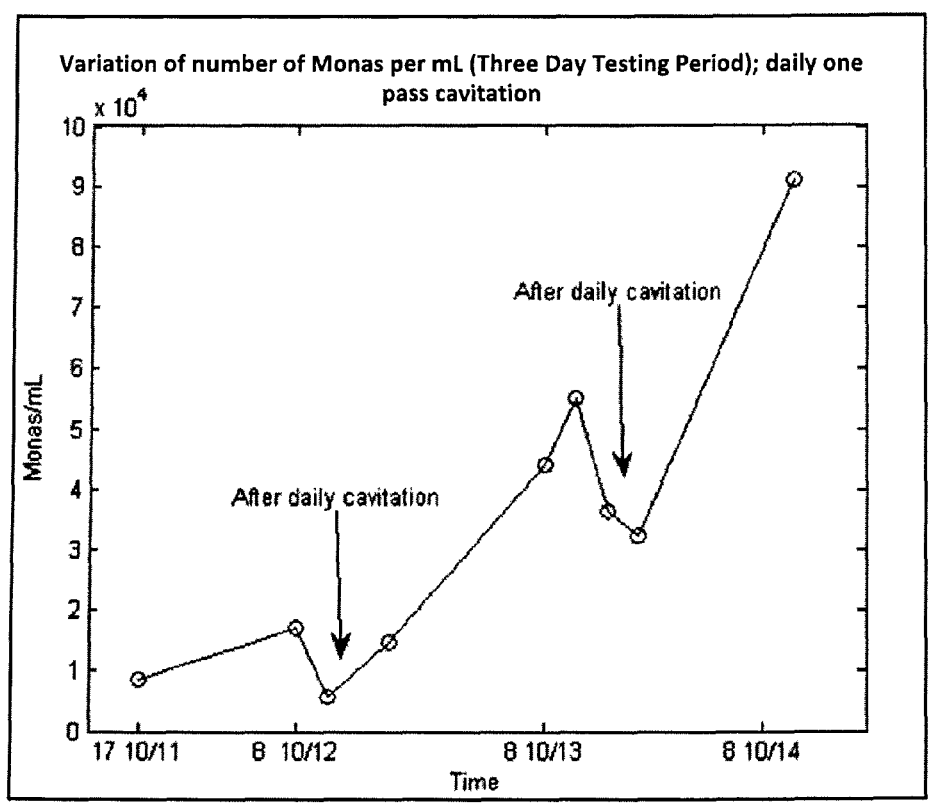
FIG. 6 of the drawings is a graph showing concentration of Monas per milliliter versus time after daily cavitation.

FIG. 6 of the drawings is a graph showing concentration of Monas per milliliter versus time after daily cavitation for the second micropond D3, and the third micropond MP5 (as described in connection with FIG. 5). In order to investigate the effect of daily cavitation on productivity, cavitation was induced daily for twelve minutes in the third micropond MP5 and the second micropond D3. Daily productivity of micropond MP5 (i.e. the clean pond) was about six grams per meter squared. The second micropond D3 was still contaminated due to the high applied cavitation number as shown in FIG. 6.

As a result of the daily cavitation of one pass with 31 pounds per square inch, which was applied to the second micropond D3 for three days, the second micropond D3 did not crash and survived for four days before the inventors used its algae cultivation fluid for new experiments.

Figure 7:
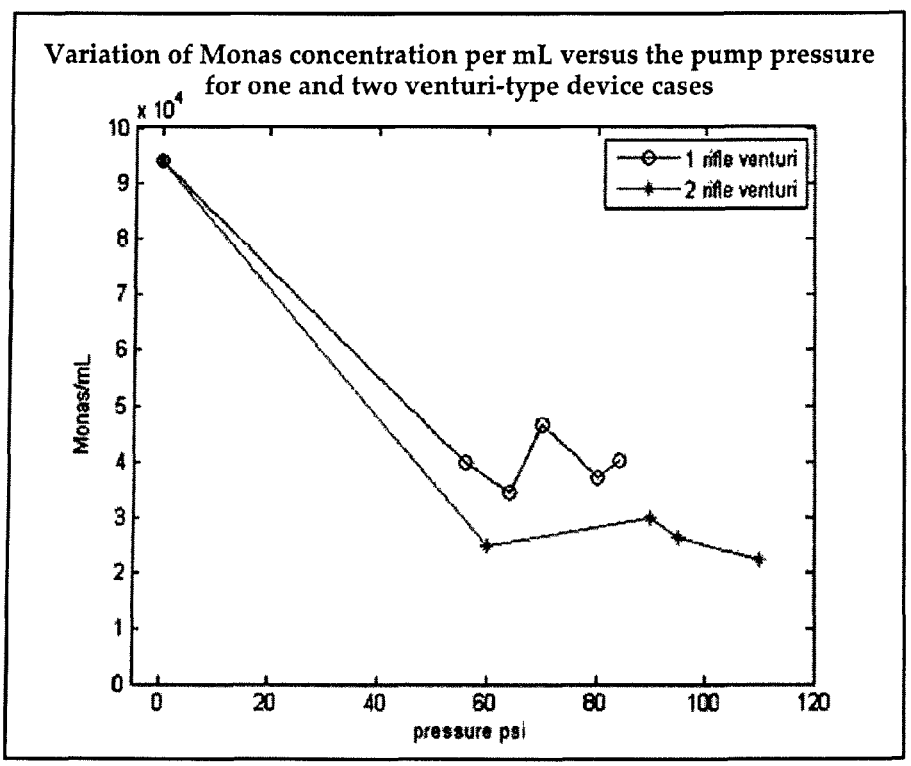
FIG. 7 of the drawings is a graph showing Monas per milliliter versus downstream pump pressure of the algae cultivation fluid.

FIG. 7 of the drawings is a graph showing Monas per milliliter versus downstream pump pressure of the algae cultivation fluid. Contaminated algae cultivation fluid in a first micropond D3 was transferred to a second micropond D1 using both one and two rifle venturi-type devices, each device having a different cavitation number. The inventors observed that at the same pressure, the performance of the two rifle venturi-type device is better than the performance of the one rifle venturi-type device. It is interesting to note that the discharge coefficient for the two rifle venturi-type devices is 0.75, while the discharge coefficient for one rifle venturi-type device is 0.93. This illustrates that some performance is lost when two rifle venturi-type devices are in series.

Exemplary Use Case for Orifice Plate

Contaminated algae cultivation fluid was transferred from a first micropond D1 to a second micropond D3 using orifice plate FL8 (see Table 1 and Table 2) on day one. On the first day, the first micropond D1 was contaminated with 65,000 Monas. In order to clean the algae cultivation fluid, the orifice plate FL8 having the highest discharge coefficient of 0.85 was utilized. Different cavitation numbers were tested. The resulting kill rate for each cavitation number tested is depicted in FIG. 8.

Figure 8:
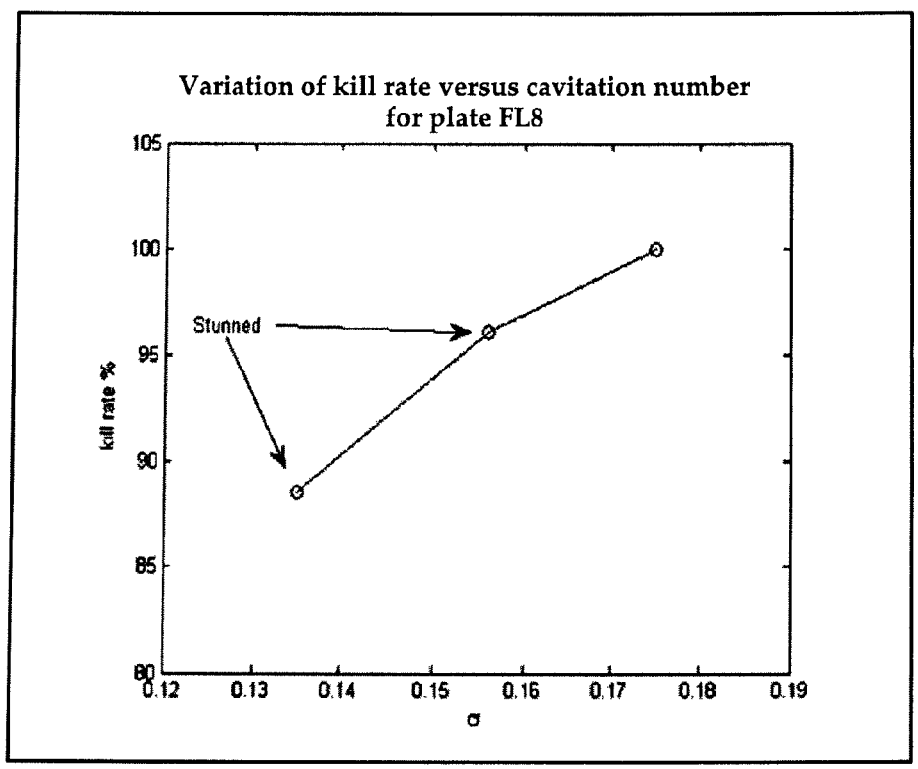
FIG. 8 of the drawings is a graph showing kill rate percentages versus cavitation number.

FIG. 8 of the drawings is a graph showing kill rate percentages versus cavitation number. The inventors observed that the Monas were stunned in the cases with kill rates less than 100 percent. The inventors also observed that very high kill rates may be achieved with cavitation numbers less than 0.18. The second micropond D3 in the experiment was free of Monas on day two, and remained clean for at least the next four days. The inventors concluded that by having higher discharge coefficients, cavitation numbers of 0.18 may be achieved while utilizing less energy.

Overall Review of Exemplary Use Cases

The inventors observed that venturi-type cavitation devices having discharge coefficients of 0.93 and higher, and cavitation plates FL8 and FL9 having discharge coefficients of 0.82 and higher, performed better than the other devices tested.

The inventors observed that tests showed plate FL8 kills all grazers when cavitation numbers are below 0.18 and when pump pressures are 110 pounds per square inch and greater. With an appropriately sized pump, cavitation numbers of 0.18 with only 85 psi of pump pressure may be achieved utilizing rifle venturi-type cavitation devices. In addition to achieving higher discharge coefficients, the flow discharging ability of the cavitation apparatus with the rifle venturi-type cavitation devices had fewer amounts of residual bubbles than the exemplary cases utilizing orifice plates. This indicates that more gas bubbles collapse in the rifle venturi-type cavitation devices, which can be a sign of better performance as the collapsing bubbles are believed to be responsible at least in part for the elimination of the grazers.

Based on the experiments described herein, the inventors believe the following three approaches are efficacious:

1. Inducing hydrodynamic cavitation with low intensity (cavitation numbers of approximately 0.3 and pump pressure of about 60 pounds per square inch) with discharge into the same pond may kill up to 70% of the grazers and hurt and stun the rest with one pass. Additional dilution may remove the stunned grazers overnight producing a clean pond the next day.

2. Transferring the algae cultivation fluid to a clean pond through a cavitation apparatus in which high intensity cavitation is induced, for example, cavitation numbers of approximately 0.18 and pump pressure of about 90 pounds per square inch for a rifle venturi-type device. If an orifice plate is utilized such as FL8 and FL9, the pressure should be about 120 pounds per square inch.

3. Two rifle venturi-type cavitation devices showed better performance than one rifle venturi-type cavitation devices with regard to pump pressure, although the combined discharge coefficient was smaller than the discharge coefficient calculated from the one single rifle venturi-type device.

The inventors have also observed that competing algae species with flagella are also removed from the algae cultivation fluid during the cavitation process. This result is surprising and unexpected, as the inventors expected the cavitation process not to eliminate competing algal species.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

The invention claimed is:

1. A method for reducing an amount of unwanted living organisms within an algae cultivation fluid, the algae cultivation fluid including wanted living algae of genus *Nannochloropsis*, the method comprising:
   subjecting the algae cultivation fluid, the algae cultivation fluid including the wanted living algae of genus *Nannochloropsis* and the amount of unwanted living organisms, to an amount of cavitation, the amount of cavitation being defined by a pressure differential between a downstream pressure and a vapor pressure, the pressure differential between the downstream pressure and the vapor pressure divided by half of a product of a fluid density multiplied by a square of a velocity of an apparatus throat, the amount of cavitation falling within a range of 0.05 to 1 and the amount of cavitation reducing the amount of the unwanted living organisms within the algae cultivation fluid without significantly reducing the wanted living algae of genus *Nannochloropsis*.

2. The method according to claim 1, further comprising selectively varying the amount of cavitation within the range to selectively control the amount of unwanted living organisms within the algae cultivation fluid.

3. The method according to claim 1, further comprising selecting the amount of cavitation within the range based upon the type of unwanted living organisms within the algae cultivation fluid.

4. The method according to claim 1, wherein the type of unwanted living organisms includes any of rotifers, cryptomonads, larval copepods, gnathostomulids, monerans, spirotrichs, or combinations thereof.

5. The method according to claim 1, wherein the apparatus throat includes one or more orifices of an orifice plate.

6. The method according to claim 5, wherein the orifice plate includes a central orifice disposed in axial alignment with a central axis of the orifice plate and a plurality of intermediate orifices spaced apart from and disposed in an arcuate pattern around the central axis.

7. The method according to claim 6, wherein the central orifice includes a substantially frusto-conical geometrical configuration having a sidewall disposed at approximately a twenty degree angle relative to the central axis of the orifice plate, further wherein one or more of the plurality of intermediate orifices includes the same geometrical configuration as the central orifice.

8. The method according to claim 1, wherein the apparatus throat includes a venturi throat of a venturi-type device, the venturi throat being disposed between a convergent nozzle and a divergent nozzle.

9. The method according to claim 8, further comprising the step of causing the algae cultivation fluid to swirl before the algae cultivation fluid enters the convergent nozzle of the venturi-type device.

10. The method according to claim 1, further comprising executing the method according to a predetermined schedule.

11. The method according to claim 1, further comprising the steps of receiving the untreated algae cultivation fluid from an algae cultivation fluid source and providing the treated algae cultivation fluid to the algae cultivation fluid source after the step of subjecting.

12. The method according to claim 11, further comprising the step of diluting the treated algae cultivation fluid provided to the algae cultivation fluid source with a dilutive fluid after the step of providing.

13. The method according to claim 1, further comprising re-subjecting the algae cultivation fluid to an additional amount of cavitation by passing the algae cultivation fluid through a second apparatus throat positioned downstream of a first apparatus throat.

14. An improved method for producing a biofuel from algae cultivation fluid, the algae cultivation fluid including algae of genus *Nannochloropsis*, the method comprising:
   reducing an amount of unwanted living organisms within the algae cultivation fluid, the algae cultivation fluid including algae of genus *Nannochloropsis*, by passing the algae cultivation fluid through at least one apparatus throat to induce an amount of cavitation within the algae cultivation fluid to reduce the unwanted living organisms within the algae cultivation fluid;
   wherein reducing the amount of unwanted living organisms within an algae cultivation fluid causes algae cells within the algae cultivation fluid to mature at an accelerated rate relative to algae cells within algae cultivation fluid having a higher concentration of unwanted living organisms;
   separating algae cells from the algae cultivation fluid; and
   processing the algae cells in such a way that a biofuel is produced.

15. The method according to claim 14, further comprising monitoring the amount of unwanted living organisms within the algae cultivation fluid to determine an appropriate time to perform the step of reducing.

16. The method according to claim 14, further comprising the step of diluting the algae cultivation fluid with an additional fluid to further reduce the amount of unwanted living organisms within the algae cultivation fluid.

* * * * *